United States Patent [19]
Powell

[11] Patent Number: 6,110,723
[45] Date of Patent: Aug. 29, 2000

[54] YFII PSEUDOURIDINE SYNTHASE

[75] Inventor: David J. Powell, Radnor, Pa.

[73] Assignee: SmithKline Beecham Corporation, Philadelphia, Pa.

[21] Appl. No.: 09/190,821

[22] Filed: Nov. 12, 1998

[51] Int. Cl.[7] .............................. C12N 9/90; C07H 21/04
[52] U.S. Cl. ................ 435/233; 435/183; 435/252.3; 435/252.33; 435/320.1; 536/23.1; 536/23.2; 536/23.7
[58] Field of Search ...................... 435/233, 183, 435/252.3, 252.33, 320.1; 536/23.1, 23.2, 23.7

[56] References Cited

FOREIGN PATENT DOCUMENTS 0786519  7/1997  European Pat. Off. .

OTHER PUBLICATIONS

SwissProt Submission, Accession No. P33643, Direct Submission, Feb. 1, 1994.
SwissProt Submission, Accession No. Q45480, Direct Submission, Nov. 1, 1997.
Arigoni, et al., "A Genome–based Approach for the Identification of Essential Bacterial Genes", *Nature Biotechnology*, vol. 16, pp. 851–856, Sep. 1998.
Kammen, et al.: "Pufification, Structure and Properties of Escherichia Coli tRNA Pseudouridine Synthetase I." *Journal of Biological Chemistry*, Vol. 263, No.5, pp. 2255–2263, Feb. 15,1988.
Conrad, et al.: "The rluC Gene of Eshirichia Coli Codes for a Pseudouridine Synthetase that is Solely Responsible for Synthesis of Pseudouridine at Position 955, 2504, and 2580 in 23 Ribosomal RNA." *Journal of Biological Chemistry*, Vol. 273, No. 29, pp. 18562–18566, Jul. 17, 1998.
Lecointe, et al.: "Characterization of Yeast Protein Deg 1 as Pseudouridine Synthetase (Pus3) Catalyzing the Formation Of Ψ39 in tRNA Anticodon Loop." *Journal of Biological Chemistry*, Vol. 273. No. 3, pp. 1316–1323, Jan. 16, 1988.

*Primary Examiner*—Ponnathapu Achutamurthy
*Assistant Examiner*—Nashaat T. Nashed
*Attorney, Agent, or Firm*—Edward R. Gimmi; Thomas S. Deibert; William T. King

[57] ABSTRACT

The invention provides YfiI pseudouridine synthase polypeptides and polynucleotides encoding YfiI pseudouridine synthase polypeptides and methods for producing such polypeptides by recombinant techniques. Also provided are methods for utilizing YfiI pseudouridine synthase polypeptides to screen for antibacterial compounds.

26 Claims, No Drawings

SEQUENCE LISTING

```
<160> NUMBER OF SEQ ID NOS: 2

<210> SEQ ID NO 1
<211> LENGTH: 1266
<212> TYPE: DNA
<213> ORGANISM: Staphylococcus aureus
<220> FEATURE:
<221> NAME/KEY: CDS
<222> LOCATION: (119)...(1033)
<221> NAME/KEY: misc_feature
<222> LOCATION: (1)...(1266)
<223> OTHER INFORMATION: n = A,T,C or G

<400> SEQUENCE: 1
ttggttatga ttttccaata tttaatatag cagattcaag tttaacaatt ggtgtaatat      60
taattattat tgccttatta aaggatactt ccaataaaaa ggagaaggag gttaagta       118 atg gag act tat gaa ttt aac att aca gat aaa gaa caa aca ggt atg      166
Met Glu Thr Tyr Glu Phe Asn Ile Thr Asp Lys Glu Gln Thr Gly Met
 1               5                   10                  15
```

-continued

| | | |
|---|---|---|
| cgt gta gat aag ttg ctg cct gaa tta aat aat gat tgg tct cgt aac<br>Arg Val Asp Lys Leu Leu Pro Glu Leu Asn Asn Asp Trp Ser Arg Asn<br>         20                   25                 30 | 214 |
| cag ata caa gat tgg att aaa gca ggt tta gtc gtt gca aac gat aaa<br>Gln Ile Gln Asp Trp Ile Lys Ala Gly Leu Val Val Ala Asn Asp Lys<br>     35                  40                 45 | 262 |
| gtt gtt aaa tct aat tat aaa gtg aaa ctt aat gat cat ata gtt gtc<br>Val Val Lys Ser Asn Tyr Lys Val Lys Leu Asn Asp His Ile Val Val<br> 50                   55                 60 | 310 |
| act gaa aaa gaa gtg gtt gaa gct gac att cta cct gaa aat tta aat<br>Thr Glu Lys Glu Val Val Glu Ala Asp Ile Leu Pro Glu Asn Leu Asn<br> 65                   70                 75                 80 | 358 |
| tta gat att tat tat gaa gat gat gac gtt gca gtt gta tat aaa ccg<br>Leu Asp Ile Tyr Tyr Glu Asp Asp Val Ala Val Val Tyr Lys Pro<br>               85                 90                 95 | 406 |
| aaa ggc atg gta gtt cat cca tca cca ggt cat tat acc aat aca tta<br>Lys Gly Met Val Val His Pro Ser Pro Gly His Tyr Thr Asn Thr Leu<br>             100                 105              110 | 454 |
| gtt aat ggt tta atg tat caa att aaa gat tta tcg ggt att aat gga<br>Val Asn Gly Leu Met Tyr Gln Ile Lys Asp Leu Ser Gly Ile Asn Gly<br>         115                 120              125 | 502 |
| gaa att cgt cca ggt att gtt cac cgt ata gat atg gat act tct ggt<br>Glu Ile Arg Pro Gly Ile Val His Arg Ile Asp Met Asp Thr Ser Gly<br> 130                  135               140 | 550 |
| tta tta atg gtt gct aaa aat gat att gct cat cgt ggg ctt gta gaa<br>Leu Leu Met Val Ala Lys Asn Asp Ile Ala His Arg Gly Leu Val Glu<br> 145                  150               155              160 | 598 |
| caa tta atg gat aaa tct gtt aaa aga aaa tat atc gct tta gtt cac<br>Gln Leu Met Asp Lys Ser Val Lys Arg Lys Tyr Ile Ala Leu Val His<br>             165                 170              175 | 646 |
| ggg aat att cct cat gat tac ggt aca atc gat gcg cca att ggt aga<br>Gly Asn Ile Pro His Asp Tyr Gly Thr Ile Asp Ala Pro Ile Gly Arg<br>               180                 185              190 | 694 |
| aac aaa aat gat cgt caa tct atg gct gtt gtt gat gat ggt aag gaa<br>Asn Lys Asn Asp Arg Gln Ser Met Ala Val Val Asp Asp Gly Lys Glu<br>         195                 200              205 | 742 |
| gca gtg aca cat ttt aac gta cta gaa cat ttt aaa gat tat acg ctt<br>Ala Val Thr His Phe Asn Val Leu Glu His Phe Lys Asp Tyr Thr Leu<br> 210                  215               220 | 790 |
| gtt gaa tgt caa ctt gaa aca gga cgt acg cat caa atc cgt gtg cac<br>Val Glu Cys Gln Leu Glu Thr Gly Arg Thr His Gln Ile Arg Val His<br> 225                  230               235              240 | 838 |
| atg aaa tat att ggc ttc cca tta gtt ggt gat cca aag tat gga ccg<br>Met Lys Tyr Ile Gly Phe Pro Leu Val Gly Asp Pro Lys Tyr Gly Pro<br>             245                 250              255 | 886 |
| aaa aag aca ttg gat att ggt ggt caa gct cta cat gct gga ctt att<br>Lys Lys Thr Leu Asp Ile Gly Gly Gln Ala Leu His Ala Gly Leu Ile<br>         260                 265              270 | 934 |
| gga ttc gac cat cca gta aca ggt gaa tat att gaa aga cat gct gaa<br>Gly Phe Asp His Pro Val Thr Gly Glu Tyr Ile Glu Arg His Ala Glu<br> 275                  280               285 | 982 |
| ata cca caa gac ttt gaa gat tta tta gat aca att cga aaa aga gat<br>Ile Pro Gln Asp Phe Glu Asp Leu Leu Asp Thr Ile Arg Lys Arg Asp<br>         290                 295              300 | 1030 |
| gca taattgtgtc gtgctataat tacgataaca ttattatgta aactataagt<br>Ala<br>305 | 1083 |
| atttatcgtt ttcgtttttt aaaaatgaaa acacattata aaatagatta aggttaacat | 1143 |

-continued

```
ttttactgag aatggntatt ttcatataga ttgacaaagc gcctgattag tattatcccc   1203
tataccagtt aagtaccacc attaagggct ttaattgagc gtccagagag acgtcaagac   1263
atg                                                                 1266
```

<210> SEQ ID NO 2
<211> LENGTH: 305
<212> TYPE: PRT
<213> ORGANISM: Staphylococcus aureus

<400> SEQUENCE: 2

```
Met Glu Thr Tyr Glu Phe Asn Ile Thr Asp Lys Glu Gln Thr Gly Met
  1               5                  10                  15

Arg Val Asp Lys Leu Leu Pro Glu Leu Asn Asn Asp Trp Ser Arg Asn
                 20                  25                  30

Gln Ile Gln Asp Trp Ile Lys Ala Gly Leu Val Val Ala Asn Asp Lys
             35                  40                  45

Val Val Lys Ser Asn Tyr Lys Val Lys Leu Asn Asp His Ile Val Val
 50                  55                  60

Thr Glu Lys Glu Val Val Glu Ala Asp Ile Leu Pro Glu Asn Leu Asn
 65                  70                  75                  80

Leu Asp Ile Tyr Tyr Glu Asp Asp Val Ala Val Val Tyr Lys Pro
                 85                  90                  95

Lys Gly Met Val Val His Pro Ser Pro Gly His Tyr Thr Asn Thr Leu
                100                 105                 110

Val Asn Gly Leu Met Tyr Gln Ile Lys Asp Leu Ser Gly Ile Asn Gly
            115                 120                 125

Glu Ile Arg Pro Gly Ile Val His Arg Ile Asp Met Asp Thr Ser Gly
        130                 135                 140

Leu Leu Met Val Ala Lys Asn Asp Ile Ala His Arg Gly Leu Val Glu
145                 150                 155                 160

Gln Leu Met Asp Lys Ser Val Lys Arg Lys Tyr Ile Ala Leu Val His
                165                 170                 175

Gly Asn Ile Pro His Asp Tyr Gly Thr Ile Asp Ala Pro Ile Gly Arg
            180                 185                 190

Asn Lys Asn Asp Arg Gln Ser Met Ala Val Val Asp Asp Gly Lys Glu
        195                 200                 205

Ala Val Thr His Phe Asn Val Leu Glu His Phe Lys Asp Tyr Thr Leu
    210                 215                 220

Val Glu Cys Gln Leu Glu Thr Gly Arg Thr His Gln Ile Arg Val His
225                 230                 235                 240

Met Lys Tyr Ile Gly Phe Pro Leu Val Gly Asp Pro Lys Tyr Gly Pro
                245                 250                 255

Lys Lys Thr Leu Asp Ile Gly Gly Gln Ala Leu His Ala Gly Leu Ile
            260                 265                 270

Gly Phe Asp His Pro Val Thr Gly Glu Tyr Ile Glu Arg His Ala Glu
        275                 280                 285

Ile Pro Gln Asp Phe Glu Asp Leu Leu Asp Thr Ile Arg Lys Arg Asp
    290                 295                 300

Ala
305
```

YFII PSEUDOURIDINE SYNTHASE

FIELD OF THE INVENTION

This invention relates to newly identified polynucleotides and polypeptides, and their production and uses, as well as their variants, agonists and antagonists, and their uses. In particular, the invention relates to polynucleotides and polypeptides of the YabO family, as well as their variants, hereinafter referred to as "YfiI pseudouridine synthase," "YfiI pseudouridine synthase polynucleotide(s)," and "YfiI pseudouridine synthase polypeptide(s)" as the case may be.

BACKGROUND OF THE INVENTION

It is particularly preferred to employ Staphylococcal genes and gene products as targets for the development of antibiotics. The Staphylococci make up a medically important genera of microbes. They are known to produce two types of disease, invasive and toxigenic. Invasive infections are characterized generally by abscess formation effecting both skin surfaces and deep tissues. S. aureus is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome. The frequency of *Staphylococcus aureus* infections has risen dramatically in the past few decades. This has been attributed to the emergence of multiply antibiotic resistant strains and an increasing population of people with weakened immune systems. It is no longer uncommon to isolate *Staphylococcus aureus* strains which are resistant to some or all of the standard antibiotics. This phenomenon has created an unmet medical need and demand for new anti-microbial agents, vaccines, drug screening methods, and diagnostic tests for this organism.

Moreover, the drug discovery process is currently undergoing a fundamental revolution as it embraces "functional genomics," that is, high throughput genome- or gene-based biology. This approach is rapidly superseding earlier approaches based on "positional cloning" and other methods. Functional genomics relies heavily on the various tools of bioinformatics to identify gene sequences of potential interest from the many molecular biology databases now available as well as from other sources. There is a continuing and significant need to identify and characterize further genes and other polynucleotides sequences and their related polypeptides, as targets for drug discovery.

Clearly, there exists a need for polynucleotides and polypeptides, such as the YfiI pseudouridine synthase embodiments of the invention, that have a present benefit of, among other things, being useful to screen compounds for antimicrobial activity. Such factors are also useful to determine their role in pathogenesis of infection, dysfunction and disease. There is also a need for identification and characterization of such factors and their antagonists and agonists to find ways to prevent, ameliorate or correct such infection, dysfunction and disease.

SUMMARY OF THE INVENTION

The present invention relates to YfiI pseudouridine synthase, in particular YfiI pseudouridine synthase polypeptides and YfiI pseudouridine synthase polynucleotides, recombinant materials and methods for their production. In another aspect, the invention relates to methods for using such polypeptides and polynucleotides, including treatment of microbial diseases, amongst others. In a further aspect, the invention relates to methods for identifying agonists and antagonists using the materials provided by the invention, and for treating microbial infections and conditions associated with such infections with the identified agonist or antagonist compounds. In a still further aspect, the invention relates to diagnostic assays for detecting diseases associated with microbial infections and conditions associated with such infections, such as assays for detecting YfiI pseudouridine synthase expression or activity.

Various changes and modifications within the spirit and scope of the disclosed invention will become readily apparent to those skilled in the art from reading the following descriptions and from reading the other parts of the present disclosure.

DESCRIPTION OF THE INVENTION

The invention relates to YfiI pseudouridine synthase polypeptides and polynucleotides as described in greater detail below. In particular, the invention relates to polypeptides and polynucleotides of a YfiI pseudouridine synthase of *Staphylococcus aureus*, which is related by amino acid sequence homology to *E.coli* YfiI, *B.subtilis* YlyB polypeptide. The invention relates especially to YfiI pseudouridine synthase having the nucleotide and amino acid sequences set out in Table 1 as SEQ ID NO:1 and SEQ ID NO:2 respectively. Note that sequences recited in the Sequence Listing below as "DNA" represent an exemplification of the invention, since those of ordinary skill will recognize that such sequences can be usefully employed in polynucleotides in general, including ribopolynucleotides.

TABLE 1

YfiI pseudouridine synthase Polynucleotide and Polypeptide Sequences (A) *Staphylococcus aureus* YfiI pseudouridine synthase polynucleotide sequence [SEQ ID NO:1].

5'-
TTGGTTATGATTTTCCAATATTTAATATAGCAGATTCAAGTTTAACAATTGGTGTAATATTAATTATTATTG

CCTTATTAAAGGATACTTCCAATAAAAAGGAGAAGGAGGTTAAGTAATGGAGACTTATGAATTTAACATTAC

AGATAAAGAACAAACAGGTATGCGTGTAGATAAGTTGCTGCCTGAATTAAATAATGATTGGTCTCGTAACCA

GATACAAGATTGGATTAAAGCAGGTTTAGTCGTTGCAAACGATAAAGTTGTTAAATCTAATTATAAAGTGAA

TABLE 1-continued

YfiI pseudouridine synthase Polynucleotide and Polypeptide Sequences

ACTTAATGATCATATAGTTGTCACTGAAAAAGAAGTGGTTGAAGCTGACATTCTACCTGAAAATTTAAATTT

AGATATTTATTATGAAGATGATGACGTTGCAGTTGTATATAAACCGAAAGGCATGGTAGTTCATCCATCACC

AGGTCATTATACCAATACATTAGTTAATGGTTTAATGTATCAAATTAAAGATTTATCGGGTATTAATGGAGA

AATTCGTCCAGGTATTGTTCACCGTATAGATATGGATACTTCTGGTTTATTAATGGTTGCTAAAAATGATAT

TGCTCATCGTGGGCTTGTAGAACAATTAATGGATAAATCTGTTAAAAGAAAATATATCGCTTTAGTTCACGG

GAATATTCCTCATGATTACGGTACAATCGATGCGCCAATTGGTAGAAACAAAAATGATCGTCAATCTATGGC

TGTTGTTGATGATGGTAAGGAAGCAGTGACACATTTTAACGTACTAGAACATTTTAAAGATTATACGCTTGT

TGAATGTCAACTTGAAACAGGACGTACGCATCAAATCCGTGTGCACATGAAATATATTGGCTTCCCATTAGT

TGGTGATCCAAAGTATGGACCGAAAAAGACATTGGATATTGGTGGTCAAGCTCTACATGCTGGACTTATTGG

ATTCGACCATCCAGTAACAGGTGAATATATTGAAAGACATGCTGAAATACCACAAGACTTTGAAGATTTATT

AGATACAATTCGAAAAAGAGATGCATAATTGTGTCGTGCTATAATTACGATAACATTATTATGTAAACTATA

AGTATTTATCGTTTTCGTTTTTTAAAAATGAAAACACATTATAAAATAGATTAAGGTTAACATTTTTACTGA

GAATGGNTATTTTCATATAGATTGACAAAGCGCCTGATTAGTATTATCCCCTATACCAGTTAAGTACCACCA

TTAAGGGCTTTAATTGAGCGTCCAGAGAGACGTCAAGACATG-3'

(B) *Staphylococcus aureus* YfiI pseudouridine synthase polypeptide
sequence decuced from a polynucleotide in this table [SEQ ID NO:2].

NH$_2$-
MATYEFNITDKEQTGMRVDKLLPELNNDWSRNQIQDWIKAGLVVANDKVVKSNYKVKLNDHIVVTEKEVVEA

DILPENLNLDIYYEDDDVAVVYKPKGMVVHPSPGHYTNTLVNGLMYQIKDLSGINGEIRPGIVHRIDMDTSG

LLMVAKNDIAHRGLVEQLMDKSVKRRYIALVHGNIPHDYGTIDAPIGRNKNDRQSMAVVDDGKEAVTHFNVL

EHFKDYTLVECQLETGRTHQIRVHMKYIGFPLVGDPKYGPKKTLDIGGQALHAGLIGFDHPTTGEYIERHAE

IPQDFEDLLDTIRKRDA-COOH

Deposited Materials

A deposit containing a *Staphylococcus aureus* WCUH 29 strain has been deposited with the National Collections of Industrial and Marine Bacteria Ltd. (herein "NCIMB"), 23 St. Machar Drive, Aberdeen AB2 1RY, Scotland on Sep. 11, 1995 and assigned NCIMB Deposit No. 40771, and referred to as *Staphylococcus aureus* WCUH29 on deposit. . The *Staphylococcus aureus* strain deposit is referred to herein as "the deposited strain" or as "the DNA of the deposited strain."

The deposited strain contains a full length YfiI pseudouridine synthase gene. The sequence of the polynucleotides contained in the deposited strain, as well as the amino acid sequence of any polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The deposited strain will be irrevocably and without restriction or condition released to the public upon the issuance of a patent. The deposited strain is provided merely as convenience to those of skill in the art and is not an admission that a deposit is required for enablement, such as that required under 35 U.S.C. §112. A license may be required to make, use or sell the deposited strain, and compounds derived therefrom, and no such license is hereby granted.

In one aspect of the invention there is provided an isolated nucleic acid molecule encoding a mature polypeptide expressible by the *Staphylococcus aureus* WCUH 29 strain, which polypeptide is contained in the deposited strain. Further provided by the invention are YfiI pseudouridine synthase polynucleotide sequences in the deposited strain, such as DNA and RNA, and amino acid sequences encoded thereby. Also provided by the invention are YfiI pseudouridine synthase polypeptide and polynucleotide sequences isolated from the deposited strain.

Polypeptides

YfiI pseudouridine synthase polypeptide of the invention is substantially phylogenetically related to other proteins of the YabO family.

In one aspect of the invention there are provided polypeptides of *Staphylococcus aureus* referred to herein as "YfiI pseudouridine synthase" and "YfiI pseudouridine synthase polypeptides" as well as biologically, diagnostically, prophylactically, clinically or therapeutically useful variants thereof, and compositions comprising the same.

Among the particularly preferred embodiments of the invention are variants of YfiI pseudouridine synthase polypeptide encoded by naturally occurring alleles of the YfiI pseudouridine synthase gene.

The present invention further provides for an isolated polypeptide which: (a) comprises or consists of an amino acid sequence which has at least 70% identity, preferably at least 80% identity, more preferably at least 90% identity, yet more preferably at least 95% identity, most preferably at least 97–99% or exact identity, to that of SEQ ID NO:2 over the entire length of SEQ ID NO:2; (b) a polypeptide encoded by an isolated polynucleotide comprising or consisting of a polynucleotide sequence which has at least 70% identity, preferably at least 80% identity, more preferably at least 90% identity, yet more preferably at least 95% identity, even more preferably at least 97–99% or exact identity to SEQ ID NO:1 over the entire length of SEQ ID NO:1, or the entire length of that portion of SEQ ID NO:1 that encodes SEQ ID NO:2; (c) a polypeptide encoded by an isolated polynucleotide comprising or consisting of a polynucleotide sequence encoding a polypeptide which has at least 70% identity, preferably at least 80% identity, more preferably at least 90% identity, yet more preferably at least 95% identity, even more preferably at least 97–99% or exact identity, to the amino acid sequence of SEQ ID NO:2, over the entire length of SEQ ID NO:2.

The polypeptides of the invention include a polypeptide of Table 1 [SEQ ID NO:2] (in particular the mature polypeptide) as well as polypeptides and fragments, particularly those which have the biological activity of YfiI pseudouridine synthase, and also those which have at least 70% identity to a polypeptide of Table 1 [SEQ ID NO:1] or the relevant portion, preferably at least 80% identity to a polypeptide of Table 1 [SEQ ID NO:2 and more preferably at least 90% identity to a polypeptide of Table 1 [SEQ ID NO:2] and still more preferably at least 95% identity to a polypeptide of Table 1 [SEQ ID NO:2] and also include portions of such polypeptides with such portion of the polypeptide generally containing at least 30 amino acids and more preferably at least 50 amino acids.

The invention also includes a polypeptide consisting of or comprising a polypeptide of the formula:

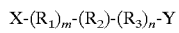

$$X\text{-}(R_1)_m\text{-}(R_2)\text{-}(R_3)_n\text{-}Y$$

wherein, at the amino terminus, X is hydrogen, a metal or any other moiety described herein for modified polypeptides, and at the carboxyl terminus, Y is hydrogen, a metal or any other moiety described herein for modified polypeptides, $R_1$ and $R_3$ are any amino acid residue or modified amino acid residue, m is an integer between 1 and 1000 or zero, n is an integer between 1 and 1000 or zero, and $R_2$ is an amino acid sequence of the invention, particularly an amino acid sequence selected from Table 1 or modified forms thereof. In the formula above, $R_2$ is oriented so that its amino terminal amino acid residue is at the left, covalently bound to $R_1$, and its carboxy terminal amino acid residue is at the right, covalently bound to $R_3$. Any stretch of amino acid residues denoted by either $R_1$ or $R_3$, where m and/or n is greater than 1, may be either a heteropolymer or a homopolymer, preferably a heteropolymer. Other preferred embodiments of the invention are provided where m is an integer between 1 and 50, 100 or 500, and n is an integer between 1 and 50, 100, or 500.

It is most preferred that a polypeptide of the invention is derived from *Staphylococcus aureus*, however, it may preferably be obtained from other organisms of the same taxonomic genus. A polypeptide of the invention may also be obtained, for example, from organisms of the same taxonomic family or order.

A fragment is a variant polypeptide having an amino acid sequence that is entirely the same as part but not all of any amino acid sequence of any polypeptide of the invention. As with YfiI pseudouridine synthase polypeptides, fragments may be "free-standing," or comprised within a larger polypeptide of which they form a part or region, most preferably as a single continuous region in a single larger polypeptide.

Preferred fragments include, for example, truncation polypeptides having a portion of an amino acid sequence of Table 1 [SEQ ID NO:2], or of variants thereof, such as a continuous series of residues that includes an amino- and/or carboxyl-terminal amino acid sequence. Degradation forms of the polypeptides of the invention produced by or in a host cell, particularly a *Staphylococcus aureus*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:2, or an isolated polypeptide comprising an amino acid sequence having at least 15, 20, 30, 40, 50 or 100 contiguous amino acids truncated or deleted from the amino acid sequence of SEQ ID NO:2.

Also preferred are biologically active fragments which are those fragments that mediate activities of YfiI pseudouridine synthase, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of *Staphylococcus aureus* or the ability to initiate, or maintain cause Disease in an individual, particularly a human.

Fragments of the polypeptides of the invention may be employed for producing the corresponding full-length polypeptide by peptide synthesis; therefore, these variants may be employed as intermediates for producing the full-length polypeptides of the invention.

In addition to the standard single and triple letter representations for amino acids, the term "X" or "Xaa" may also be used in describing certain polypeptides of the invention. "X" and "Xaa" mean that any of the twenty naturally occurring amino acids may appear at such a designated position in the polypeptide sequence.

Polynucleotides

It is an object of the invention to provide polynucleotides that encode YfiI pseudouridine synthase polypeptides, particularly polynucleotides that encode the polypeptide herein designated YfiI pseudouridine synthase.

In a particularly preferred embodiment of the invention the polynucleotide comprises a region encoding YfiI pseudouridine synthase polypeptides comprising a sequence set out in Table 1 [SEQ ID NO:1] which includes a full length gene, or a variant thereof. The Applicants believe that this full length gene is essential to the growth and/or survival of an organism which possesses it, such as *Staphylococcus aureus*.

As a further aspect of the invention there are provided isolated nucleic acid molecules encoding and/or expressing YfiI pseudouridine synthase polypeptides and polynucleotides, particularly *Staphylococcus aureus* YfiI pseudouridine synthase polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof and compositions comprising the same.

Another aspect of the invention relates to isolated polynucleotides, including at least one full length gene, that encodes a YfiI pseudouridine synthase polypeptide having a deduced amino acid sequence of Table 1 [SEQ ID NO:2] and polynucleotides closely related thereto and variants thereof.

In another particularly preferred embodiment of the invention there is a YfiI pseudouridine synthase polypeptide from *Staphylococcus aureus* comprising or consisting of an amino acid sequence of Table 1 [SEQ ID NO:2], or a variant thereof.

Using the information provided herein, such as a polynucleotide sequence set out in Table 1 [SEQ ID NO:1], a polynucleotide of the invention encoding YfiI pseudouridine synthase polypeptide may be obtained using standard cloning and screening methods, such as those for cloning and sequencing chromosomal DNA fragments from bacteria using *Staphylococcus aureus* WCUH 29 cells as starting material, followed by obtaining a full length clone. For example, to obtain a polynucleotide sequence of the invention, such as a polynucleotide sequence given in Table 1 [SEQ ID NO:1], typically a library of clones of chromosomal DNA of *Staphylococcus aureus* WCUH 29 in *E.coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in Table 1 [SEQ ID NO:1] was discovered in a DNA library derived from *Staphylococcus aureus* WCUH 29.

Moreover, each DNA sequence set out in Table 1 [SEQ ID NO:1] contains an open reading frame encoding a protein having about the number of amino acid residues set forth in Table 1 [SEQ ID NO:2] with a deduced molecular weight that can be calculated using amino acid residue molecular weight values well known to those skilled in the art. The polynucleotide of SEQ ID NO:1, between nucleotide number 119 and the stop codon which begins at nucleotide number 1034 of SEQ ID NO:1, encodes the polypeptide of SEQ ID NO:2.

In a further aspect, the present invention provides for an isolated polynucleotide comprising or consisting of: (a) a polynucleotide sequence which has at least 70% identity, preferably at least 80% identity, more preferably at least 90% identity, yet more preferably at least 95% identity, even more preferably at least 97–99% or exact identity to SEQ ID NO:1 over the entire length of SEQ ID NO:1; (b) a polynucleotide sequence encoding a polypeptide which has at least 70% identity, preferably at least 80% identity, more preferably at least 90% identity, yet more preferably at least 95% identity, even more preferably at least 97–99% or 100% exact, to the amino acid sequence of SEQ ID NO:2, over the entire length of SEQ ID NO:2.

A polynucleotide encoding a polypeptide of the present invention, including homologs and orthologs from species other than *Staphylococcus aureus*, may be obtained by a process which comprises the steps of screening an appropriate library under stringent hybridization conditions with a labeled or detectable probe consisting of or comprising the sequence of SEQ ID NO:1 or a fragment thereof, and isolating a full-length gene and/or genomic clones containing said polynucleotide sequence.

The invention provides a polynucleotide sequence identical over its entire length to a coding sequence (open reading frame) in Table 1 [SEQ ID NO:1]. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or preproprotein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

A preferred embodiment of the invention is a polynucleotide of consisting of or comprising nucleotide 119 to the nucleotide immediately upstream of or including nucleotide 1034 set forth in SEQ ID NO:1 of Table 1, both of which encode the YfiI pseudouridine synthase polypeptide.

The invention also includes a polynucleotide consisting of or comprising a polynucleotide of the formula:

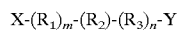

wherein, at the 5' end of the molecule, X is hydrogen, a metal or a modified nucleotide residue, or together with Y defines a covalent bond, and at the 3' end of the molecule, Y is hydrogen, a metal, or a modified nucleotide residue, or together with X defines the covalent bond, each occurrence of $R_1$ and $R_3$ is independently any nucleic acid residue or modified nucleic acid residue, m is an integer between 1 and 3000 or zero, n is an integer between 1 and 3000 or zero, and $R_2$ is a nucleic acid sequence or modified nucleic acid sequence of the invention, particularly a nucleic acid sequence selected from Table 1 or a modified nucleic acid sequence thereof. In the polynucleotide formula above, $R_2$ is oriented so that its 5' end nucleic acid residue is at the left, bound to $R_1$, and its 3' end nucleic acid residue is at the right, bound to R₃. Any stretch of nucleic acid residues denoted by either $R_1$ and/or $R_2$, where m and/or n is greater than 1, may be either a heteropolymer or a homopolymer, preferably a heteropolymer. Where, in a preferred embodiment, X and Y together define a covalent bond, the polynucleotide of the above formula is a closed, circular polynucleotide, which can be a double-stranded polynucleotide wherein the formula shows a first strand to which the second strand is complementary. In another preferred embodiment m and/or n is an integer between 1 and 1000. Other preferred embodiments of the invention are provided where m is an integer between 1 and 50, 100 or 500, and n is an integer between 1 and 50, 100, or 500.

It is most preferred that a polynucleotide of the invention is derived from *Staphylococcus aureus*, however, it may preferably be obtained from other organisms of the same taxonomic genus. A polynucleotide of the invention may also be obtained, for example, from organisms of the same taxonomic family or order.

The term "polynucleotide encoding a polypeptide" as used herein encompasses polynucleotides that include a sequence encoding a polypeptide of the invention, particularly a bacterial polypeptide and more particularly a polypeptide of the *Staphylococcus aureus* YfiI pseudouridine synthase having an amino acid sequence set out in Table 1 [SEQ ID NO:2]. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of Table 1 [SEQ ID NO:2]. Fragments of a polynucleotides of the invention may be used, for example, to synthesize full-length polynucleotides of the invention.

Further particularly preferred embodiments are polynucleotides encoding YfiI pseudouridine synthase variants, that have the amino acid sequence of YfiI pseudouridine synthase polypeptide of Table 1 [SEQ ID NO:2] in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of YfiI pseudouridine synthase polypeptide.

Further preferred embodiments of the invention are polynucleotides that are at least 70% identical over their entire length to a polynucleotide encoding YfiI pseudouridine synthase polypeptide having an amino acid sequence set out in Table 1 [SEQ ID NO:2], and polynucleotides that are complementary to such polynucleotides. Alternatively, most highly preferred are polynucleotides that comprise a region that is at least 80% identical over its entire length to a polynucleotide encoding YfiI pseudouridine synthase polypeptide and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of Table 1 [SEQ ID NO:1].

In accordance with certain preferred embodiments of this invention there are provided polynucleotides that hybridize, particularly under stringent conditions, to YfiI pseudouridine synthase polynucleotide sequences, such as those polynucleotides in Table 1.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 micrograms/ml of denatured, sheared salmon sperm DNA, followed by washing the hybridization support in 0.1× SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:1 under stringent hybridization conditions with a probe having the sequence of said polynucleotide sequence set forth in SEQ ID NO:1 or a fragment thereof, and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding YfiI pseudouridine synthase and to isolate cDNA and genomic clones of other genes that have a high identity, particularly high sequence identity, to the YfiI pseudouridine synthase gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have lee than 30 nucleotide residues or base pairs.

A coding region of a YfiI pseudouridine synthase gene may be isolated by screening using a DNA sequence provided in Table 1 [SEQ ID NO:1] to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., *PNAS USA* 85: 8998–9002, 1988).

Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of Table 1 [SEQ ID NOS:1 or 2] may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems which comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., BASIC METHODS IN MOLECULAR BIOLOGY, (1986) and Sambrook, et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococci, staphylococci, enterococci *E. coli*, streptomyces, cyanobacteria, *Bacillus subtilis*, and *Staphylococcus aureus*; fungal cells, such as cells of a yeast, Kluveromyces, Saccharomyces, a basidiomycete, *Candida albicans* and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic, Prognostic, Serotyping and Mutation Assays

This invention is also related to the use of YfiI pseudouridine synthase polynucleotides and polypeptides of the invention for use as diagnostic reagents. Detection of YfiI pseudouridine synthase polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the YfiI pseudouridine synthase gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled YfiI pseudouridine synthase polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science*, 230: 1242 (1985). Sequence changes at specific locations also may be revealed by nuclease protection assays, such as RNase, V1 and S1 protection assay or a chemical cleavage method. See, for example, Cotton et al., *Proc. Natl. Acad. Sci., USA*, 85: 4397–4401 (1985).

In another embodiment, an array of oligonucleotides probes comprising YfiI pseudouridine synthase nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., *Science*, 274: 610 (1996)).

Thus in another aspect, the present invention relates to a diagnostic kit which comprises: (a) a polynucleotide of the present invention, preferably the nucleotide sequence of SEQ ID NO:1, or a fragment thereof; (b) a nucleotide sequence complementary to that of (a); (c) a polypeptide of the present invention, preferably the polypeptide of SEQ ID NO:2 or a fragment thereof; or (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a Disease, among others.

This invention also relates to the use of polynucleotides of the present invention as diagnostic reagents. Detection of a mutated form of a polynucleotide of the invention, preferable, SEQ ID NO:1, which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

The nucleotide sequences of the present invention are also valuable for organism chromosome identification. The sequence is specifically targeted to, and can hybridize with, a particular location on an organism's chromosome, particularly to a *Staphylococcus aureus* chromosome. The mapping of relevant sequences to chromosomes according to the present invention may be an important step in correlating those sequences with pathogenic potential and/or an ecological niche of an organism and/or drug resistance of an organism, as well as the essentiality of the gene to the organism. Once a sequence has been mapped to a precise chromosomal location, the physical position of the sequence on the chromosome can be correlated with genetic map data. Such data may be found on-line in a sequence database. The relationship between genes and diseases that have been mapped to the same chromosomal region are then identified through known genetic methods, for example, through linkage analysis (coinheritance of physically adjacent genes) or mating studies, such as by conjugation.

The differences in a polynucleotide and/or polypeptide sequence between organisms possessing a first phenotype and organisms possessing a different, second different phenotype can also be determined. If a mutation is observed in some or all organisms possessing the first phenotype but not in any organisms possessing the second phenotype, then the mutation is likely to be the causative agent of the first phenotype.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR. As an example, PCR primers complementary to a polynucleotide encoding YfiI pseudouridine synthase polypeptide can be used to identify and analyze mutations. These primers may be used for, among other things, amplifying YfiI pseudouridine synthase DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing, disease, preferably bacterial infections, more preferably infections caused by *Staphylococcus aureus*, comprising determining from a sample derived from an individual, such as a bodily material, an increased level of expression of polynucleotide having a sequence of Table 1 [SEQ ID NO:1]. Increased or decreased expression of a YfiI pseudouridine synthase polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of YfiI pseudouridine synthase polypeptide compared to normal control tissue samples may be used to detect the presence of an infection, for example. Assay techniques that can be used to determine levels of a YfiI pseudouridine synthase polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

Differential Expression

The polynucleotides and polynucleotides of the invention may be used as reagents for differential screening methods. There are many differential screening and differential display methods known in the art in which the polynucleotides and polypeptides of the invention may be used. For example, the differential display technique is described by Chuang et al., *J. Bacteriol.* 175:2026–2036 (1993). This method identifies those genes which are expressed in an organism by identifying mRNA present using randomly-primed RT-PCR. By comparing pre-infection and post infection profiles, genes up and down regulated during infection can be identified and the RT-PCR product sequenced and matched to ORF "unknowns."

In Vivo Expression Technology (IVET) is described by Camilli et al., *Proc. Nat'l. Acad. Sci. USA.* 91:2634–2638 (1994). IVET identifies genes up-regulated during infection when compared to laboratory cultivation, implying an important role in infection. ORFs identified by this technique are implied to have a significant role in infection establishment and/or maintenance. In this technique random chromosomal fragments of target organism are cloned upstream of a promoter-less recombinase gene in a plasmid vector. This construct is introduced into the target organism which carries an antibiotic resistance gene flanked by resolvase sites. Growth in the presence of the antibiotic removes from the population those fragments cloned into the plasmid vector capable of supporting transcription of the recombinase gene and therefore have caused loss of antibiotic resistance. The resistant pool is introduced into a host and at various times after infection bacteria may be recovered and assessed for the presence of antibiotic resistance. The chromosomal fragment carried by each antibiotic sensitive bacterium should carry a promoter or portion of a gene normally upregulated during infection. Sequencing upstream of the recombinase gene allows identification of the up regulated gene.

RT-PCR may also be used to analyze gene expression patterns. For RT PCR using the polynucleotides of the invention, messenger RNA is isolated from bacterial infected tissue, e.g., 48 hour murine lung infections, and the amount of each mRNA species assessed by reverse transcription of the RNA sample primed with random hexanucleotides followed by PCR with gene specific primer pairs. The determination of the presence and amount of a particular mRNA species by quantification of the resultant PCR product provides information on the bacterial genes which are transcribed in the infected tissue. Analysis of gene transcription can be carried out at different times of infection to gain a detailed knowledge of gene regulation in bacterial pathogenesis allowing for a clearer understanding of which gene products represent targets for screens for antibacterials. Because of the gene specific nature of the PCR primers employed it should be understood that the bacterial mRNA preparation need not be free of mammalian RNA. This allows the investigator to carry out a simple and quick RNA preparation from infected tissue to obtain bacterial mRNA species which are very short lived in the bacterium (in the order of 2 minute halflives). Optimally the bacterial mRNA is prepared from infected murine lung tissue by mechanical disruption in the presence of TRIzole (GIBCO-BRL) for very short periods of time, subsequent processing according to the manufacturers of TRIzole reagent and DNAase treatment to remove contaminating DNA. Preferably the process is optimized by finding those conditions which give a maximum amount of *Staphylococcus aureus* 16S ribosomal RNA as detected by probing Northerns with a suitably labeled sequence specific oligonucleotide probe. Typically a 5' dye labeled primer is used in each PCR primer pair in a PCR reaction which is terminated optimally between 8 and 25 cycles. The PCR products are separated on 6% polyacrylamide gels with detection and quantification using GeneScanner (manufactured by ABI).

Gridding and Polynucleotide Subtraction

Methods have been described for obtaining information about gene expression and identity using so called "high density DNA arrays" or grids. See, e.g., M. Chee et al., *Science,* 274:610–614 (1996) and other references cited therein. Such gridding assays have been employed to identify certain novel gene sequences, referred to as Expressed Sequence Tags (EST) (Adams et a., *Science,* 252:1651–1656 (1991)). A variety of techniques have also been described for identifying particular gene sequences on the basis of their gene products. For example, see International Patent Application No. WO91/07087, published May 30, 1991. In addition, methods have been described for the amplification of desired sequences. For example, see International Patent Application No. WO91/17271, published Nov. 14, 1991.

The polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as using hybridization or nucleic acid amplification, using a probes obtained or derived from a bodily sample, to determine the presence of a particular polynucleotide sequence or related sequence in an individual. Such a presence may indicate the presence of a pathogen, particularly *Staphylococcus aureus*, and may be useful in diagnosing and/or prognosing disease or a course of disease. A grid comprising a number of variants of the polynucleotide sequence of SEQ ID NO:1 are preferred. Also preferred is a comprising a number of variants of a polynucleotide sequence encoding the polypeptide sequence of SEQ ID NO:2.

Antibodies

The polypeptides and polynucleotides of the invention or variants thereof, or cells expressing the same can be used as immunogens to produce antibodies immunospecific for such polypeptides or polynucleotides respectively.

In certain preferred embodiments of the invention there are provided antibodies against YfiI pseudouridine synthase polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495–497 (1975); Kozbor et al., *Immunology Today* 4: 72 (1983); Cole et al., pg. 77–96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms such as other mammals, may be used to express humanized antibodies immunospecific to the polypeptides or polynucleotides of the invention.

Alternatively, phage display technology may be utilized to select antibody genes with binding activities towards a polypeptide of the invention either from repertoires of PCR amplified v-genes of lymphocytes from humans screened for possessing anti-YfiI pseudouridine synthase or from naive libraries (McCafferty, et al., (1990), Nature 348, 552–554; Marks, et al., (1992) *Biotechnology* 10, 779–783). The affinity of these antibodies can also be improved by, for example, chain shuffling (Clackson et al., (1991) *Nature* 352: 628).

The above-described antibodies may be employed to isolate or to identify clones expressing the polypeptides or polynucleotides of the invention to purify the polypeptides or polynucleotides by, for example, affinity chromatography.

Thus, among others, antibodies against YfiI pseudouridine synthase-polypeptide or YfiI pseudouridine synthase-polynucleotide may be employed to treat infections, particularly bacterial infections.

Polypeptide variants include antigenically, epitopically or immunologically equivalent variants form a particular aspect of this invention.

A polypeptide or polynucleotide of the invention, such as an antigenically or immunologically equivalent derivative or a fusion protein of the polypeptide is used as an antigen to immunize a mouse or other animal such as a rat or chicken. The fusion protein may provide stability to the polypeptide. The antigen may be associated, for example by conjugation, with an immunogenic carrier protein for example bovine serum albumin, keyhole limpet haemocyanin or tetanus toxoid. Alternatively, a multiple antigenic polypeptide comprising multiple copies of the polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized," where the complimentarily determining region or regions of the hybridoma-derived antibody has been transplanted into a human monoclonal antibody, for example as described in Jones et al. (1986), *Nature* 321, 522–525 or Tempest et al., (1991) *Biotechnology* 9, 266–273.

In accordance with an aspect of the invention, there is provided the use of a polynucleotide of the invention for therapeutic or prophylactic purposes, in particular genetic immunization. Among the particularly preferred embodiments of the invention are naturally occurring allelic variants of YfiI pseudouridine synthase polynucleotides and polypeptides encoded thereby.

The use of a polynucleotide of the invention in genetic immunization will preferably employ a suitable delivery method such as direct injection of plasmid DNA into muscles (Wolff et al., *Hum Mol Genet* (1992) 1: 363, Manthorpe et al., *Hum. Gene Ther.* (1983) 4: 419), delivery of DNA complexed with specific protein carriers (Wu et al., *J Biol Chem.* (1989) 264: 16985), coprecipitation of DNA with calcium phosphate (Benvenisty & Reshef, *PNAS USA*, (1986) 83: 9551), encapsulation of DNA in various forms of liposomes (Kaneda et al., *Science* (1989) 243: 375), particle bombardment (Tang et al., *Nature* (1992) 356:152, Eisenbraun et al., *DNA Cell Biol* (1993) 12: 791) and in vivo infection using cloned retroviral vectors (Seeger et al., *PNAS USA* (1984) 81: 5849).

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

Polypeptides and polynucleotides of the present invention are responsible for many biological functions, including many disease states, in particular the Diseases hereinbefore mentioned. It is therefore desirable to devise screening methods to identify compounds which stimulate or which inhibit the function of the polypeptide or polynucleotide. Accordingly, in a further aspect, the present invention provides for a method of screening compounds to identify those which stimulate or which inhibit the function of a polypeptide or polynucleotide of the invention, as well as related polypeptides and polynucleotides. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of YfiI pseudouridine synthase polypeptides and polynucleotides; or may be structural or functional mimetics thereof (see Coligan et al., *Current Protocols in Immunology* 1(2):Chapter 5 (1991)).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention, to form a mixture, measuring YfiI pseudouridine synthase polypeptide and/or polynucleotide activity in the mixture, and comparing the YfiI pseudouridine synthase polypeptide and/or polynucleotide activity of the mixture to a standard. Fusion proteins, such as those made from Fc portion and YfiI pseudouridine synthase polypeptide, as hereinbefore described, can also be used for high-throughput screening assays to identify antagonists of the polypeptide of the present invention, as well as of phylogenetically and and/or functionally related polypeptides (see D. Bennett et al., J Mol Recognition, 8:52–58 (1995); and K. Johanson et al., J Biol Chem, 270(16) :9459–9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of YfiI pseudouridine synthase polypeptides or polynucleotides, particularly those compounds that are bacteristatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising YfiI pseudouridine synthase polypeptide and a labeled substrate or ligand of such polypeptide is incubated in the absence or the presence of a candidate molecule that may be a YfiI pseudouridine synthase agonist or antagonist. The ability of the candidate molecule to agonize or antagonize the YfiI pseudouridine synthase polypeptide is reflected in decreased binding of the labeled ligand or decreased production of product from such substrate. Molecules that bind gratuitously, i.e., without inducing the effects of YfiI pseudouridine synthase polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to colorimetric, labeled substrate converted into product, a reporter gene that is responsive to changes in YfiI pseudouridine synthase polynucleotide or polypeptide activity, and binding assays known in the art.

Polypeptides of the invention may be used to identify membrane bound or soluble receptors, if any, for such polypeptide, through standard receptor binding techniques known in the art. These techniques include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (e.g., cells, cell membranes, cell supernatants, tissue extracts, bodily materials). Other methods include biophysical techniques such as surface plasmon resonance and spectroscopy. These screening methods may also be used to identify agonists and antagonists of the polypeptide which compete with the binding of the polypeptide to its receptor(s), if any. Standard methods for conducting such assays are well understood in the art.

The fluorescence polarization value for a fluorescently-tagged molecule depends on the rotational correlation time or tumbling rate. Protein complexes, such as formed by YfiI pseudouridine synthase polypeptide associating with another YfiI pseudouridine synthase polypeptide or other polypeptide, labeled to comprise a fluorescently-labeled molecule will have higher polarization values than a fluorescently labeled monomeric protein. It is preferred that this method be used to characterize small molecules that disrupt polypeptide complexes.

Fluorescence energy transfer may also be used characterize small molecules that interfere with the formation of YfiI pseudouridine synthase polypeptide dimers, trimers, tetramers or higher order structures, or structures formed by YfiI pseudouridine synthase polypeptide bound to another polypeptide. YfiI pseudouridine synthase polypeptide can be labeled with both a donor and acceptor fluorophore. Upon mixing of the two labeled species and excitation of the donor fluorophore, fluorescence energy transfer can be detected by observing fluorescence of the acceptor. Compounds that block dimerization will inhibit fluorescence energy transfer.

Surface plasmon resonance can be used to monitor the effect of small molecules on YfiI pseudouridine synthase polypeptide self-association as well as an association of YfiI pseudouridine synthase polypeptide and another polypeptide or small molecule. YfiI pseudouridine synthase polypeptide can be coupled to a sensor chip at low site density such that covalently bound molecules will be monomeric. Solution protein can then passed over the YfiI pseudouridine synthase polypeptide-coated surface and specific binding can be detected in real-time by monitoring the change in resonance angle caused by a change in local refractive index. This technique can be used to characterize the effect of small molecules on kinetic rates and equilibrium binding constants for YfiI pseudouridine synthase polypeptide self-association as well as an association of YfiI pseudouridine synthase polypeptide and another polypeptide or small molecule.

A scintillation proximity assay may be used to characterize the interaction between an association of YfiI pseudouridine synthase polypeptide with another YfiI pseudouridine synthase polypeptide or a different polypeptide. YfiI pseudouridine synthase polypeptide can be coupled to a scintillation-filled bead. Addition of radio-labeled YfiI pseudouridine synthase polypeptide results in binding where the radioactive source molecule is in close proximity to the scintillation fluid. Thus, signal is emitted upon YfiI pseudouridine synthase polypeptide binding and compounds that prevent YfiI pseudouridine synthase polypeptide self-association or an association of YfiI pseudouridine synthase polypeptide and another polypeptide or small molecule will diminish signal.

ICS biosensors have been described by AMBRI (Australian Membrane Biotechnology Research Institute). They couple the self-association of macromolecules to the closing of gramacidin-facilitated ion channels in suspended membrane bilayers and hence to a measurable change in the admittance (similar to impedance) of the biosensor. This approach is linear over six decades of admittance change and is ideally suited for large scale, high through-put screening of small molecule combinatorial libraries.

In other embodiments of the invention there are provided methods for identifying compounds which bind to or otherwise interact with and inhibit or activate an activity or expression of a polypeptide and/or polynucleotide of the invention comprising: contacting a polypeptide and/or polynucleotide of the invention with a compound to be screened under conditions to permit binding to or other interaction between the compound and the polypeptide and/or polynucleotide to assess the binding to or other interaction with the compound, such binding or interaction preferably being associated with a second component capable of providing a detectable signal in response to the binding or interaction of the polypeptide and/or polynucleotide with the compound; and determining whether the compound binds to or otherwise interacts with and activates or inhibits an activity or expression of the polypeptide and/or polynucleotide by detecting the presence or absence of a signal generated from the binding or interaction of the compound with the polypeptide and/or polynucleotide.

Another example of an assay for YfiI pseudouridine synthase agonists is a competitive assay that combines YfiI pseudouridine synthase and a potential agonist with YfiI pseudouridine synthase-binding molecules, recombinant YfiI pseudouridine synthase binding molecules, natural substrates or ligands, or substrate or ligand mimetics, under appropriate conditions for a competitive inhibition assay. YfiI pseudouridine synthase can be labeled, such as by radioactivity or a colorimetric compound, such that the number of YfiI pseudouridine synthase molecules bound to a binding molecule or converted to product can be determined accurately to assess the effectiveness of the potential antagonist.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing YfiI pseudouridine synthase-induced activities, thereby preventing the action or expression of YfiI pseudouridine synthase polypeptides and/or polynucleotides by excluding YfiI pseudouridine synthase polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLE-OTIDES AS ANTISENSE INHIBITORS OF GENE EXPRESSION*, CRC Press, Boca Raton, Fla. (1988), for a description of these molecules). Preferred potential antagonists include compounds related to and variants of YfiI pseudouridine synthase.

Other examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Certain of the polypeptides of the invention are biomimetics, functional mimetics of the natural YfiI pseudouridine synthase polypeptide. These functional mimetics may be used for, among other things, antagonizing the activity of YfiI pseudouridine synthase polypeptide or as a antigen or immunogen in a manner described elsewhere herein. Functional mimetics of the polypeptides of the invention include but are not limited to truncated polypeptides. For example, preferred functional mimetics include, a polypeptide comprising the polypeptide sequence set forth in SEQ ID NO:2 lacking 20, 30, 40, 50, 60, 70 or 80 amino- or carboxy-terminal amino acid residues, including fusion proteins comprising one or more of these truncated sequences. Polynucleotides encoding each of these functional mimetics may be used as expression cassettes to express each mimetic polypeptide. It is preferred that these cassettes comprise 5' and 3' restriction sites to allow for a convenient means to ligate the cassettes together when desired. It is further preferred that these cassettes comprise gene expression signals known in the art or described elsewhere herein.

Thus, in another aspect, the present invention relates to a screening kit for identifying agonists, antagonists, ligands, receptors, substrates, enzymes, etc. for a polypeptide and/or polynucleotide of the present invention; or compounds which decrease or enhance the production of such polypeptides and/or polynucleotides, which comprises: (a) a polypeptide and/or a polynucleotide of the present invention; (b) a recombinant cell expressing a polypeptide and/or polynucleotide of the present invention; (c) a cell membrane expressing a polypeptide and/or polynucleotide of the present invention; or (d) antibody to a polypeptide and/or polynucleotide of the present invention;
which polypeptide is preferably that of SEQ ID NO:2, and which polynucleotide is preferably that of SEQ ID NO:1.

It will be appreciated that in any such kit, (a), (b), (c) or (d) may comprise a substantial component.

It will be readily appreciated by the skilled artisan that a polypeptide and/or polynucleotide of the present invention may also be used in a method for the structure-based design of an agonist, antagonist or inhibitor of the polypeptide and/or polynucleotide, by: (a) determining in the first instance the three-dimensional structure of the polypeptide and/or polynucleotide, or complexes thereof; (b) deducing the three-dimensional structure for the likely reactive site(s), binding site(s) or motif(s) of an agonist, antagonist or inhibitor; (c) synthesizing candidate compounds that are predicted to bind to or react with the deduced binding site(s), reactive site(s), and/or motif(s); and (d) testing whether the candidate compounds are indeed agonists, antagonists or inhibitors.

It will be further appreciated that this will normally be an iterative process, and this iterative process may be performed using automated and computer-controlled steps.

In a further aspect, the present invention provides methods of treating abnormal conditions such as, for instance, a Disease, related to either an excess of, an under-expression of, an elevated activity of, or a decreased activity of YfiI pseudouridine synthase polypeptide and/or polynucleotide.

If the expression and/or activity of the polypeptide and/or polynucleotide is in excess, several approaches are available. One approach comprises administering to an individual in need thereof an inhibitor compound (antagonist) as herein described, optionally in combination with a pharmaceutically acceptable carrier, in an amount effective to inhibit the function and/or expression of the polypeptide and/or polynucleotide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide and/or polynucleotide may be administered. Typical examples of such competitors include fragments of the YfiI pseudouridine synthase polypeptide and/or polypeptide.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

In still another approach, expression of the gene encoding endogenous YfiI pseudouridine synthase polypeptide can be inhibited using expression blocking techniques. This blocking may be targeted against any step in gene expression, but is preferably targeted against transcription and/or translation. An examples of a known technique of this sort involve the use of antisense sequences, either internally generated or separately administered (see, for example, O'Connor, *J Neurochem* (1991) 56:560 in Oligodeoxynucleotides as Antisense Inhibitors of Gene Expression, CRC Press, Boca Raton, Fla. (1988)). Alternatively, oligonucleotides which form triple helices with the gene can be supplied (see, for example, Lee et al., *Nucleic Acids Res* (1979) 6:3073; Cooney et al., *Science* (1988) 241:456; Dervan et al., *Science* (1991) 251:1360). These oligomers can be administered per se or the relevant oligomers can be expressed in vivo.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial YfiI pseudouridine synthase proteins that mediate tissue damage and/or; to block the normal progression of pathogenesis in infections initiated other than by the implantation of in-dwelling devices or by other surgical techniques.

In accordance with yet another aspect of the invention, there are provided YfiI pseudouridine synthase agonists and antagonists, preferably bacteristatic or bactericidal agonists and antagonists.

The antagonists and agonists of the invention may be employed, for instance, to prevent, inhibit and/or treat diseases.

*Helicobacter pylori* (herein "*H. pylori*") bacteria infect the stomachs of over one-third of the world's population causing stomach cancer, ulcers, and gastritis (International Agency for Research on Cancer (1994) *Schistosomes, Liver Flukes and Helicobacter Pylori* (International Agency for Research on Cancer, Lyon, France, http://www.uicc.ch/ecp/ecp2904.htm). Moreover, the International Agency for Research on Cancer recently recognized a cause-and-effect relationship between *H. pylori* and gastric adenocarcinoma, classifying the bacterium as a Group I (definite) carcinogen. Preferred antimicrobial compounds of the invention (agonists and antagonists of YfiI pseudouridine synthase polypeptides and/or polynucleotides) found using screens provided by the invention, or known in the art, particularly narrow-spectrum antibiotics, should be useful in the treatment of *H. pylori* infection. Such treatment should decrease the advent of *H. pylori*-induced cancers, such as gastrointestinal carcinoma. Such treatment should also prevent, inhibit and/or cure gastric ulcers and gastritis.

Vaccines

There are provided by the invention, products, compositions and methods for assessing YfiI pseudouridine synthase expression, treating disease, assaying genetic variation, and administering a YfiI pseudouridine synthase polypeptide and/or polynucleotide to an organism to raise an immunological response against a bacteria, especially a *Staphylococcus aureus* bacteria.

Another aspect of the invention relates to a method for inducing an immunological response in an individual, particularly a mammal which comprises inoculating the individual with YfiI pseudouridine synthase polynucleotide and/ or polypeptide, or a fragment or variant thereof, adequate to produce antibody and/or T cell immune response to protect said individual from infection, particularly bacterial infection and most particularly *Staphylococcus aureus* infection. Also provided are methods whereby such immunological response slows bacterial replication. Yet another aspect of the invention relates to a method of inducing immunological response in an individual which comprises delivering to such individual a nucleic acid vector, sequence or ribozyme to direct expression of YfiI pseudouridine synthase polynucleotide and/or polypeptide, or a fragment or a variant thereof, for expressing YfiI pseudouridine synthase polynucleotide and/or polypeptide, or a fragment or a variant thereof in vivo in order to induce an immunological response, such as, to produce antibody and/or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect of the invention relates to an immunological composition that when introduced into an individual, preferably a human, capable of having induced within it an immunological response, induces an immunological response in such individual to a YfiI pseudouridine synthase polynucleotide and/or polypeptide encoded therefrom, wherein the composition comprises a recombinant YfiI pseudouridine synthase polynucleotide and/or polypeptide encoded therefrom and/or comprises DNA and/or RNA which encodes and expresses an antigen of said YfiI pseudouridine synthase polynucleotide, polypeptide encoded therefrom, or other polypeptide of the invention. The immunological response may be used therapeutically or prophylactically and may take the form of antibody immunity and/or cellular immunity, such as cellular immunity arising from CTL or CD4+ T cells.

A YfiI pseudouridine synthase polypeptide or a fragment thereof may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, preferably further comprises an antigenic co-protein, such as lipoprotein D from *Hemophilus influenzae*, Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of the first protein.

Provided by this invention are compositions, particularly vaccine compositions, and methods comprising the polypeptides and/or polynucleotides of the invention and immunostimulatory DNA sequences, such as those described in Sato, Y. et al. *Science* 273: 352 (1996).

Also, provided by this invention are methods using the described polynucleotide or particular fragments thereof, which have been shown to encode non-variable regions of bacterial cell surface proteins, in polynucleotide constructs used in such genetic immunization experiments in animal models of infection with *Staphylococcus aureus*. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *Staphylococcus aureus* infection, in mammals, particularly humans.

A polypeptide of the invention may be used as an antigen for vaccination of a host to produce specific antibodies which protect against invasion of bacteria, for example by blocking adherence of bacteria to damaged tissue. Examples of tissue damage include wounds in skin or connective tissue caused, for example, by mechanical, chemical, thermal or radiation damage or by implantation of indwelling devices, or wounds in the mucous membranes, such as the mouth, throat, mammary glands, urethra or vagina.

The invention also includes a vaccine formulation which comprises an immunogenic recombinant polypeptide and/or polynucleotide of the invention together with a suitable carrier, such as a pharmaceutically acceptable carrier. Since the polypeptides and polynucleotides may be broken down in the stomach, each is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteristatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain YfiI pseudouridine synthase polypeptides and polynucleotides, it is to be understood that this covers fragments of the naturally occurring polypeptides and polynucleotides, and similar polypeptides and polynucleotides with additions, deletions or substitutions which do not substantially affect the immunogenic properties of the recombinant polypeptides or polynucleotides.

Compositions, Kits and Administration

In a further aspect of the invention there are provided compositions comprising a YfiI pseudouridine synthase polynucleotide and/or a YfiI pseudouridine synthase polypeptide for administration to a cell or to a multicellular organism.

The invention also relates to compositions comprising a polynucleotide and/or a polypeptides discussed herein or their agonists or antagonists. The polypeptides and polynucleotides of the invention may be employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides, polynucleotides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist during penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides, polynucleotides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *Staphylococcus aureus* wound infections.

Many orthopedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 μg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Sequence Databases, Sequences in a Tangible Medium, and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as GCC.

The polynucleotide and polypeptide sequences of the invention are particularly useful as components in databases useful for search analyses as well as in sequence analysis algorithms. As used in this section entitled "Sequence Databases, Sequences in a Tangible Medium, and Algorithms," and in claims related to this section, the terms "polynucleotide of the invention" and "polynucleotide sequence of the invention" mean any detectable chemical or physical characteristic of a polynucleotide of the invention that is or may be reduced to or stored in a tangible medium, preferably a computer readable form. For example, chromatographic scan data or peak data, photographic data or scan data therefrom, called bases, and mass spectrographic data. As used in this section entitled Databases and Algorithms and in claims related thereto, the terms "polypeptide of the invention" and "polypeptide sequence of the invention" mean any detectable chemical or physical characteristic of a polypeptide of the invention that is or may be reduced to or stored in a tangible medium, preferably a computer readable form. For example, chromatographic scan data or peak data, photographic data or scan data therefrom, and mass spectrographic data.

The invention provides a computer readable medium having stored thereon polypeptide sequences of the invention and/or polynucleotide sequences of the invention. For example, a computer readable medium is provided comprising and having stored thereon a member selected from the group consisting of: a polynucleotide comprising the sequence of a polynucleotide of the invention; a polypeptide comprising the sequence of a polypeptide sequence of the invention; a set of polynucleotide sequences wherein at least one of the sequences comprises the sequence of a polynucleotide sequence of the invention; a set of polypeptide sequences wherein at least one of the sequences comprises the sequence of a polypeptide sequence of the invention; a data set representing a polynucleotide sequence comprising the sequence of polynucleotide sequence of the invention; a data set representing a polynucleotide sequence encoding a polypeptide sequence comprising the sequence of a polypeptide sequence of the invention; a polynucleotide comprising the sequence of a polynucleotide sequence of the invention; a polypeptide comprising the sequence of a polypeptide sequence of the invention; a set of polynucleotide sequences wherein at least one of the sequences comprises the sequence of a polynucleotide sequence of the invention; a set of polypeptide sequences wherein at least one of said sequences comprises the sequence of a polypeptide sequence of the invention; a data set representing a polynucleotide sequence comprising the sequence of a polynucleotide sequence of the invention; a data set representing a polynucleotide sequence encoding a polypeptide sequence comprising the sequence of a polypeptide sequence of the invention. The computer readable medium can be any composition of matter used to store information or data, including, for example, commercially available floppy disks, tapes, chips, hard drives, compact disks, and video disks.

Also provided by the invention are methods for the analysis of character sequences or strings, particularly genetic sequences or encoded genetic sequences. Preferred methods of sequence analysis include, for example, methods of sequence homology analysis, such as identity and similarity analysis, RNA structure analysis, sequence assembly, cladistic analysis, sequence motif analysis, open reading frame determination, nucleic acid base calling, nucleic acid base trimming, and sequencing chromatogram peak analysis.

A computer based method is provided for performing homology identification. This method comprises the steps of providing a first polynucleotide sequence comprising the sequence a polynucleotide of the invention in a computer readable medium; and comparing said first polynucleotide sequence to at least one second polynucleotide or polypeptide sequence to identify homology.

A computer based method is also provided for performing homology identification, said method comprising the steps of: providing a first polypeptide sequence comprising the sequence of a polypeptide of the invention in a computer readable medium; and comparing said first polypeptide sequence to at least one second polynucleotide or polypeptide sequence to identify homology.

A computer based method is still further provided for polynucleotide assembly, said method comprising the steps of: providing a first polynucleotide sequence comprising the sequence of a polynucleotide of the invention in a computer readable medium; and screening for at least one overlapping region between said first polynucleotide sequence and at least one second polynucleotide or polypeptide sequence.

A computer based method is still further provided for polynucleotide assembly, said method comprising the steps of: providing a first polypeptide sequence comprising a polypeptide of the invention in a computer readable medium; and screening for at least one overlapping region between said first polypeptide sequence and at least one second polynucleotide or polypeptide sequence.

In another preferred embodiment of the invention there is provided a computer readable medium having stored thereon a member selected from the group consisting of: a polynucleotide comprising the sequence of SEQ ID NO:1; a polypeptide comprising the sequence of SEQ ID NO:2; a set of polynucleotide sequences wherein at least one of said sequences comprises the sequence of SEQ ID NO:1; a set of polypeptide sequences wherein at least one of said sequences comprises the sequence of SEQ ID NO:2; a data set representing a polynucleotide sequence comprising the sequence of SEQ ID NO:1; a data set representing a polynucleotide sequence encoding a polypeptide sequence comprising the sequence of SEQ ID NO:2; a polynucleotide comprising the sequence of SEQ ID NO:1; a polypeptide comprising the sequence of SEQ ID NO:2; a set of polynucleotide sequences wherein at least one of said sequences comprises the sequence of SEQ ID NO:1; a set of polypeptide sequences wherein at least one of said sequences comprises the sequence of SEQ ID NO:2; a data set representing a polynucleotide sequence comprising the sequence of SEQ ID NO:1; a data set representing a polynucleotide sequence encoding a polypeptide sequence comprising the sequence of SEQ ID NO:2. A further preferred embodiment of the invention provides a computer based method for performing homology identification, said method comprising the steps of providing a polynucleotide sequence comprising the sequence of SEQ ID NO:1 in a computer readable medium; and comparing said polynucleotide sequence to at least one polynucleotide or polypeptide sequence to identify homology.

A still further preferred embodiment of the invention provides a computer based method for performing homology identification, said method comprising the steps of: providing a polypeptide sequence comprising the sequence of SEQ ID NO:2 in a computer readable medium; and comparing said polypeptide sequence to at least one polynucleotide or polypeptide sequence to identify homology.

A further embodiment of the invention provides a computer based method for polynucleotide assembly, said method comprising the steps of: providing a first polynucleotide sequence comprising the sequence of SEQ ID NO:1 in a computer readable medium; and screening for at least one overlapping region between said first polynucleotide sequence and a second polynucleotide sequence.

A further embodiment of the invention provides a computer based method for performing homology identification, said method comprising the steps of: providing a polynucleotide sequence comprising the sequence of SEQ ID NO:1 in a computer readable medium; and comparing said polynucleotide sequence to at least one polynucleotide or polypeptide sequence to identify homology.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

GLOSSARY

The following definitions are provided to facilitate understanding of certain terms used frequently herein.

"Antibody(ies)" as used herein includes polyclonal and monoclonal antibodies, chimeric, single chain, and humanized antibodies, as well as Fab fragments, including the products of an Fab or other immunoglobulin expression library.

"Antigenically equivalent derivative(s)" as used herein encompasses a polypeptide, polynucleotide, or the equivalent of either which will be specifically recognized by certain bodies which, when raised to the protein, polypeptide or polynucleotide according to the invention, interferes with the immediate physical interaction between pathogen and mammalian host.

"Bispecific antibody(ies)" means an antibody comprising at least two antigen binding domains, each domain directed against a different epitope.

"Bodily material(s) means any material derived from an individual or from an organism infecting, infesting or inhabiting an individual, including but not limited to, cells, tissues and waste, such as, bone, blood, serum, cerebrospinal fluid, semen, saliva, muscle, cartilage, organ tissue, skin, urine, stool or autopsy materials.

"Disease(s)" means any disease caused by or related to infection by a bacteria, including, for example, disease, such as, infections of the upper respiratory tract (e.g., otitis media, bacterial tracheitis, acute epiglottiis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis).

"Fusion protein(s)" refers to a protein encoded by two, often unrelated, fused genes or fragments thereof. In one example, EP-A-0464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232262]. On the other hand, for some uses it would be desirable to be able to delete the Fc part after the fusion protein has been expressed, detected and purified.

"Host cell(s)" is a cell which has been transformed or transfected, or is capable of transformation or transfection by an exogenous polynucleotide sequence.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48. 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following: Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following: Algorithm: Needleman and Wunsch, J. Mol Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:1, that is it may be 100% identical, or it may include up to a certain integer number of nucleic acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leqq x_n - (x_n \cdot y),$$

wherein $n_n$ is the number of nucleic acid alterations, $x_n$ is the total number of nucleic acids in SEQ ID NO:1, y is, for instance 0.70 for 70%, 0.80 for 80%, 0.85 for 85% etc., · is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leqq x_a - (x_a \cdot y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leqq x_a - (x_a \cdot y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Immunologically equivalent derivative(s)" as used herein encompasses a polypeptide, polynucleotide, or the equivalent of either which when used in a suitable formulation to raise antibodies in a vertebrate, the antibodies act to interfere with the immediate physical interaction between pathogen and mammalian host.

"Immunospecific" means that characteristic of an antibody whereby it possesses substantially greater affinity for the polypeptides of the invention or the polynucleotides of the invention than its affinity for other related polypeptides or polynucleotides respectively, particularly those polypeptides and polynucleotides in the prior art.

"Individual(s)" means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Organism(s)" means a (i) prokaryote, including but not limited to, a member of the genus Streptococcus, Staphylococcus, Bordetella, Corynebacterium, Mycobacterium, Neisseria, Haemophilus, Actimomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia and Mycoplasma, and further including, but not limited to, a member of the species or group, Group A Streptococcus, Group B Streptococcus, Group C Streptococcus, Group D Streptococcus, Group G Streptococcus, *Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobocterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi,* Bordetella, *Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsii* and *Chlamydia trachomitis*, (ii) an archaeon, including but not limited to Archaebacter, and (iii) a unicellular or filamentous eukaryote, including but not limited to, a protozoan, a fungus, a member of the genus Saccharomyces, Kluveromyces, or Candida, and a member of the species *Saccharomyces ceriviseae, Kluveromyces lactis*, or *Candida albicans.*

"Polynucleotide(s)" generally refers to any polyribonucleotide or polydeoxyribonucleotide, which may be unmodified RNA or DNA or modified RNA or DNA, "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W. H. Freeman and Company, New York (1993) and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., *Meth. Enzymol.* 182:626–646 (1990) and Rattan et al., *Protein Synthesis: Posttranslational Modifications and Aging,* Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Recombinant expression system(s)" refers to expression systems or portions thereof or polynucleotides of the invention introduced or transformed into a host cell or host cell lysate for the production of the polynucleotides and polypeptides of the invention.

"Subtraction set" is one or more, but preferably less than 100, polynucleotides comprising at least one polynucleotide of the invention "Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion proteins and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. The present invention also includes include variants of each of the polypeptides of the invention, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

EXAMPLES

The examples below are carried out using standard techniques, which are well known and routine to those of skill in the art, except where otherwise described in detail. The examples are illustrative, but do not limit the invention.

Example 1

Strain Selection, Library Production and Sequencing

The polynucleotide having a DNA sequence given in Table 1 [SEQ ID NO:1] was obtained from a library of clones of chromosomal DNA of *Staphylococcus aureus* in *E. coli*. The sequencing data from two or more clones containing overlapping *Staphylococcus aureus* DNAs was used to construct the contiguous DNA sequence in SEQ ID NO:1. Libraries may be prepared by routine methods, for example: Methods 1 and 2 below.

Total cellular DNA is isolated from *Staphylococcus aureus* WCUH 29 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E.coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E.coli* infected with the packaged library. The library is amplified by standard procedures.

What is claimed is:

1. An isolated polynucleotide segment comprising a first polynucleotide sequence or the full complement of the entire length of the first polynucleotide sequence, wherein the first polynucleotide sequence encodes a polypeptide comprising the amino acid sequence set forth in SEQ ID NO:2.

2. The isolated polynucleotide segment of claim 1, wherein the isolated polynucleotide segment comprises the first polynucleotide sequence.

3. A vector comprising the isolated polynucleotide segment of claim 2.

4. An isolated host cell comprising the vector of claim 3.

5. A process for producing a polypeptide comprising the step of culturing the host cell of claim 4 under conditions sufficient for the production of the polypeptide, wherein the polypeptide is encoded by the first polynucleotide sequence.

6. The isolated polynucleotide segment of claim 1, wherein the isolated polynucleotide segment comprises the full complement of the entire length of the first polynucleotide sequence.

7. A vector comprising the isolated polynucleotide segment of claim 6.

8. An isolated host cell comprising the vector of claim 7.

9. A polynucleotide which encodes a fusion polypeptide and which includes the isolated polynucleotide segment of claim 1.

10. An isolated polynucleotide segment comprising a first polynucleotide sequence or the full complement of the entire length of the first polynucleotide sequence, wherein the first polynucleotide sequence comprises SEQ ID NO:1.

11. The isolated polynucleotide segment of claim 10, wherein the isolated polynucleotide segment comprises the first polynucleotide sequence.

12. A vector comprising the isolated polynucleotide segment of claim 11.

13. An isolated host cell comprising the vector of claim 12.

14. A process for producing a polypeptide comprising the step of culturing the host cell of claim 13 under conditions sufficient for the production of the polypeptide, wherein the polypeptide is encoded by the first polynucleotide sequence.

15. The isolated polynucleotide segment of claim 10, wherein the isolated polynucleotide segment comprises the full complement of the entire length of the first polynucleotide sequence.

16. A vector comprising the isolated polynucleotide segment of claim 15.

17. An isolated host cell comprising the vector of claim 16.

18. A polynucleotide which encodes a fusion polypeptide and which includes the isolated polynucleotide segment of claim 10.

19. An isolated polynucleotide segment comprising a first polynucleotide sequence or the full complement of the entire length of the first polynucleotide sequence, wherein the first polynucleotide sequence encodes a polypeptide consisting of the amino acid sequence set forth in SEQ ID NO:2.

20. The isolated polynucleotide segment of claim 19, wherein the isolated polynucleotide segment comprises the first polynucleotide sequence.

21. A vector comprising the isolated polynucleotide segment of claim 20.

22. An isolated host cell comprising the vector of claim 21.

23. A process for producing a polypeptide comprising the step of culturing the host cell of claim 22 under conditions sufficient for the production of the polypeptide, wherein the polypeptide is encoded by the first polynucleotide sequence.

24. The isolated polynucleotide segment of claim 19, wherein the isolated polynucleotide segment comprises the full complement of the entire length of the first polynucleotide sequence.

25. A vector comprising the isolated polynucleotide segment of claim 24.

26. An isolated host cell comprising the vector of claim 25.

* * * * *